United States Patent [19]
Middleton
[11] 3,963,776
[45] June 15, 1976

[54] AMINE FLUOROACYLIMIDE SURFACTANTS

[75] Inventor: William J. Middleton, Chadds Ford, Pa.

[73] Assignee: E. I. Du Pont de Nemours and Company, Wilmington, Del.

[22] Filed: June 24, 1974

[21] Appl. No.: 482,576

[52] U.S. Cl. .......... 260/561 H; 260/404.5
[51] Int. Cl.² .......... C07C 103/38
[58] Field of Search .......... 260/404.5, 561 H

[56] References Cited

UNITED STATES PATENTS

| | | | |
|---|---|---|---|
| 3,410,880 | 11/1968 | Brocklehurst | 260/404.5 |
| 3,488,389 | 1/1970 | McKillip | 260/561 H |

OTHER PUBLICATIONS

Slagel, J. Org. Chem., 33, 1374 (1968).

McKillip, Chem. Rev., 73, 261 (1973).

*Primary Examiner*—C. Davis

[57] ABSTRACT

Aqueous solutions containing from 0.001 to 1% of a surfactant composed of at least one compound of the formula

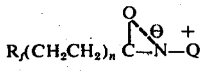

wherein $R_f$ is a straight chain fluorocarbon radical of 6 to 16 carbons, n is 0 or 1, and $Q^+$ is derived from a water-soluble tertiary amine, Q having from 3 to 6 carbon atoms and up to 3 oxygen atoms as oxa or hydroxy groups and having surface tension less than 25 dynes/cm, are disclosed.

7 Claims, No Drawings

AMINE FLUOROACYLIMIDE SURFACTANTS

BACKGROUND OF THE INVENTION

1. Field of the Invention

This invention relates to certain novel amine fluoroacylimides and to aqueous solutions containing amine fluoroacylimides having low surface tension.

2. Background of the Invention

U.S. Pat. No. 3,488,389 discloses compounds of the formula

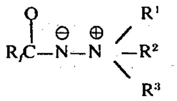

where $R_f$ is a perfluoroalkyl radical and $R^1$, $R^2$ and $R^3$ are alkyl or aryl radicals which decompose thermally to give perfluoroalkyl isocyanates. R. C. Slagel, J. Org, Chem. 33, 1374 (1968) has disclosed the reaction

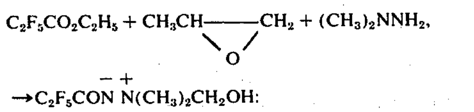

W. J. McKillip, E. A. Seder, B. M. Culbertson and S. Wawzonek, Chem. Rev., 73, 261,282 (1973), report that aminimides of $C_{12}$ through $C_{18}$ acids possess interesting surface tension or wetting properties.

U.S. Pat. No. 3,410,880 claims amine acylimides derived from higher fatty acids and discloses their use of detergents.

SUMMARY OF THE INVENTION

The present invention is directed to aqueous solutions containing from 0.001 to 1% by weight of a compound having the formula

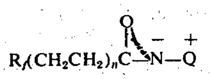

where Q is derived from a water-soluble tertiary amine having from 3 to 6 carbon atoms and up to 3 oxygen atoms in the form of oxa or hydroxy groups.

*n* is O or 1, and $R_f$ is a straight chain perfluoroalkyl radical having 6 to 16 carbon atoms;

said solution having a surface tension less than 25 dynes/cm at 25°C.

This invention also encompasses the novel compound

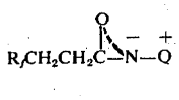

where $R_f$ and Q are defined hereinabove.

DETAILED DESCRIPTION OF THE INVENTION

It has been discovered that certain fluoroacylimides are potent surfactant materials capable of reducing the surface tension of water at 25°C. below 25 dynes/cm. In many instances solutions having a surface tension of 15 – 20 dynes/cm can be obtained. By contrast, the surface tension of hydrocarbon aminimides is about 30 dynes/cm. Accordingly, the surfactant solutions and foam made therewith are useful in fighting hydrocarbon fires.

In one aspect, this invention comprises aqueous solutions containing a surfactant composed of at least one compound of the formula

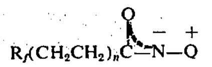

wherein $R_f$ is a straight chain perfluorocarbon radical of 6 to 16 carbons and $Q^+$ is derived from a tertiary amine Q which is miscible in water. *n* is O or 1.

Compounds within the scope of this definition where *n* = O have been disclosed by U.S. Pat. No. 3,488,389. This patent does not, however, disclose aqueous solutions of the compounds, nor does it recognize any surfactant properties.

In common with most surfactants the compounds of the present invention comprise a long chain having a hydrophilic end ($R_f$), and a hydrophilic end —CONQ. The precise structure of the tertiary amine Q is not important, but it should contain less than 6 carbon atoms and up to three oxa or hydroxy groups to meet the hydrophilic requirements. In general, the tertiary amines which meet the requirements will be soluble in water to the extent of at least 25% by weight at 25°C., preferably, in fact, miscible with water in all proportions at that temperature.

Tertiary amines in this category include trimetylamine, dimethylethylamine, dimethylethanolamine, N-methyl pyrrolidine N-2 hydroxyethyl pyrrolidine, N-methyl piperidine, methyl diethanolamine, dimethyl-2-hydroxy prophenolamine and the like. Trimethylamine is suitable and readily available and accordingly is preferred.

The compounds wherein *n* is 1, i.e., compounds of the formula

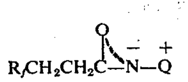

are novel compounds and are preferred in the practices of this invention since they are substantially more stable to hydrolysis than the compounds herein *n* is O, and also lower than surface tension of water to a greater degree.

The preferred values of $R_f$ are groups of the formula $F(CF_2CF_2)_n$—obtained by the oligomerization of tetrafluoroethylene, wherein *n* is 3,4,5 and 6.

The amine fluoroacylimides of this invention are prepared by treating a suitable 2-unsubstituted aminimide ($\overline{HN^{\ominus}\text{-}Q^{\oplus}}$) with an ester of an aliphatic fluorocarboxylic acid. Solvents suitable for the reaction include alcohols, such as methanol, ethanol, isopropanol, and t-butanol, and nitriles such as acetonitrile. The temperature of the reaction can be in the range between 20° and 100°. The reflux temperature of the solvent is often convenient. The amine fluoroacylimides can be isolated from the reaction mixture by evaporation of the solvent, and they can be purified if needed by conventional techniques such as recrystallization from a suitable solvent.

The 2-unsubstituted aminimides used in these preparations can be prepared by any of the known methods.

It is often convenient to prepare them in situ in the reaction solvent, and then without isolation further react them with the fluorocarboxylic ester. For example, the 2-unsubstituted aminimides can be prepared in situ by dehydrohalogenation of a 1,1,1-trialkylhydrazinium halide with a strong base, such as sodium methoxide, in an alcohol solvent. They can also be prepared in situ by the reaction of a 1,1-dialkylhydrazine with ethylene or propylene oxide in a polar solvent such as methanol, ethanol, or acetonitrile. Examples of these compounds are:

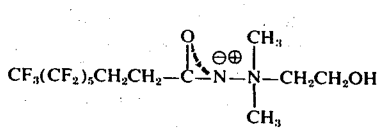

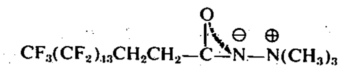

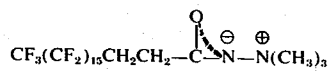

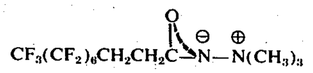

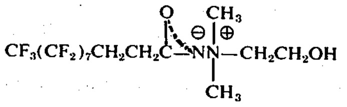

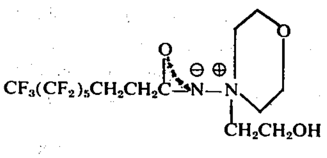

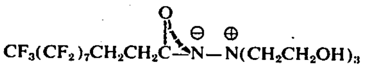

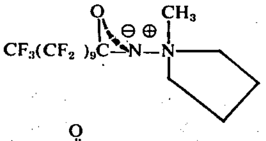

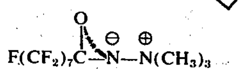

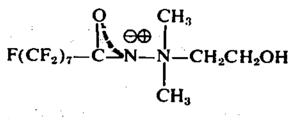

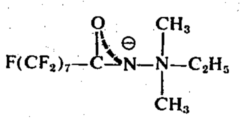

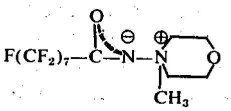

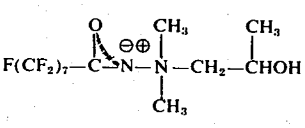

Utility

The amine fluoroacylimides of this invention and their aqueous solutions have many applications. For example, they are effective spreading agents for aqueous wax emulsions. They can also be used as wetting agents, emulsion stabilizing agents, and foaming agents. Because aqueous solutions of many of these amine fluoroacylimides have surface tensions below the surface tensions of gasoline and oil, these solutions are useful in extinguishing gasoline and oil fires when applied as a mist or foam.

Specific Embodiments of the Invention

The following examples will serve to illustrate the practice of the invention:

EXAMPLE 1

Trimethylamine 4,4,5,5,6,6,7,7,8,8,9,9,10,10,11,11,11-Heptadecafluoroundecanimide

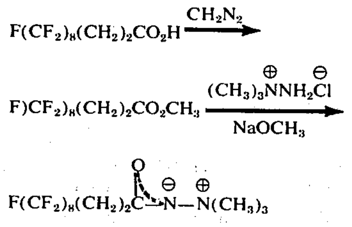

A 3% solution of diazomethane in ether was added to a solution of 3.29 g of 4,4,5,5,6,6,7,7,8,8,9,9,10,10,11,11,11-heptadecafluoroundecanoic acid in 10 ml of ether until no further reaction took place. The ether was removed by evaporation under reduced pressure, and the residue was added to a solution prepared by dissolving 0.16 g (0.0067 mole) of sodium in 10 ml methanol. 1,1,1-Trimethylhydrazinium chloride, 0.74 g (0.0067 mole), was also added, and the resulting reaction mixture was refluxed for 3 hr, cooled, and then mixed with 20 ml ether. The precipitated sodium chloride was filtered off, and the filtrate was evaporated to dryness under reduced pressure to give 2.70 g of trimethylamine 4,4,5,5,6,6,7,7,8,8,9,9,10,10,11,11,11-heptadecafluoroundecanimide as a white solid, mp 90°–94°. A soln. of 0.1% in water had a surface tension of 14.66 dynes/cm, an 0.01% solution, 14.81 dynes/cm, an 0.001% solution, 24.30 dynes/cm.

Anal. Calcd for $C_{14}H_{13}F_{17}N_2O$: C, 30.67; H, 2.39; F, 58.91; N, 5.11. Found: C, 30.38; H, 2.41; F, 58.72; N, 4.97.

EXAMPLE 2

Trimethylamine 4,4,5,5,6,6,7,7,8,8,9,9,9-Tridecafluorononanimide

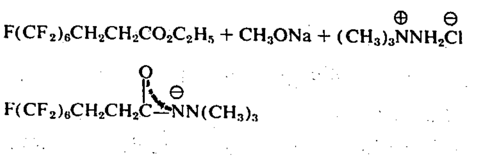

Sodium, 1.1 g (0.047 mole), was dissolved in 50 ml methanol, and 5.2 g (0.047 mole) of 1,1,1-trimethylhydrazinium chloride and 19.75 g (0.047 mole) of ethyl 4,4,5,5,6,6,7,7,8,8,9,9,9-tridecafluorononanate were added to the solution. The reaction mixture was refluxed for 18 hr. and then cooled, mixed with 50 ml ether, and filtered. The filtrate was evaporated to dryness under reduced pressure, and the residue was dissolved in hot benzene and filtered. The filtrate was evaporated to dryness under reduced pressure, and the residue was recrystallized from hexane to give 12.03 g of trimethylamine 4,4,5,5,6,6,7,7,8,8,9,9,9-tridecafluorononanimide as colorless crystals, mp 63°–65°.

Anal. Calcd for $C_{12}H_{13}F_{13}N_2O$: C, 32.15; H, 2.92; N, 6.25; H, 55.10. Found: C, 31.88; H, 2.92; N, 5.84; F, 54.84.

An 0.1% solution of this compound in water has a surface tension of 16.32 dynes/cm.

EXAMPLE 3

Trimethylamine Perfluorooctanimide

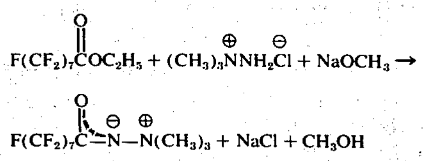

To a solution prepared by dissolving 1.15 g (0.05 g atom) of sodium in 50 ml methanol was added 5.58 g (0.05 mole) of 1,1,1-trimethylhydrazinium chloride and 22.1 g (0.05 mole) of ethyl perfluorooctanoate. The reaction mixture was refluxed for 2 hr, and then cooled and filtered. The filtrate was mixed with 50 ml ether, filtered again, and then evaporated to dryness under reduced pressure. The solid residue was recrystallized from benzene to give 17.0 g (72% yield) of trimethylamine perfluorooctanimide as colorless crystals: mp 66°–68°, ir (KBr) 6.05 μ, $^{19}F$ nmr (acetone) δ −81.2 ppm (3F), −115.7 ppm (2F), −121.7 ppm (8F) and −126.2 ppm (2F). The surface tension of an 0.1% solution in water is 16.43 dynes/cm.

Anal. Calcd for $C_{11}H_9F_{15}N_2O$: C, 28.10; H, 1.93; F, 60.61; N, 5.96. Found: C, 28.39; H, 1.93; F, 59.94; N, 5.62.

EXAMPLE 4

(2-Hydroxyethyl)dimethylamine Perfluorooctanimide

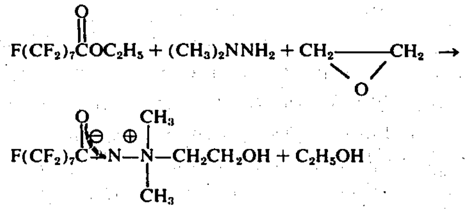

Ethylene oxide, 2.5 ml (0.05 mole) was distilled into a solution of 17.7 g (0.04 mole) of ethyl perfluorooctanoate and 3.0 g (0.05 mole) of dimethylhydrazine in 50 ml methanol, and the reaction mixture was stirred at 25° for 18 hr. The reaction mixture was then evaporated to dryness under reduced pressure to give 19.6 g (98% yield) of(2-hydroxyethyl)dimethylamine perfluorooctanimide as a viscous, colorless syrup, $n_D^{25}$ 1.3793. The surface tension of an 0.1% solution is 16.60 dynes/cm.

Anal. Calcd for $C_{12}H_{11}F_{15}N_2O_2$: N, 5.60; F, 56.97. Found: N, 5.73; F, 57.13.

EXAMPLE 5

Ethyldimethylamine Perfluorooctanimide

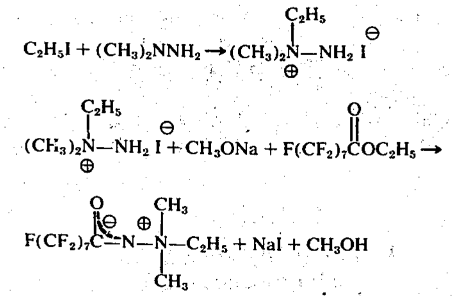

Ethyl iodide, 79.5 g (0.5 mole), was added dropwise to a solution of 30 g (0.5 mole) of dimethylhydrazine in 500 ml ether. The crystals that precipitated were collected on a filter under dry nitrogen to give 68 g of 1-ethyl-1,1-dimethylhydrazinium iodide as hygroscopic white crystals, mp 116°–120°.

Anal. Calcd for $C_4H_{13}N_2I$: C, 22.23; H, 6.06; N, 12.97. Found: C, 22.42; H, 6.16; N, 12.96.

To a solution prepared by dissolving 1.15 g (0.05 g-atom) of sodium in 50 ml methanol was added 10.2 g (0.05 mole) of the iodide and 22.1 g (0.05 mole) of ethyl perfluorooctanoate, and the reaction mixture was refluxed for 2 hr. The methanol was removed by evaporation under reduced pressure and the residue was taken up in hot benzene and filtered to remove the sodium iodide. The filtrate was evaporated under reduced pressure to give 17.1 g (71% yield) of ethyldimethylamine perfluorooctanimide as a colorless gummy residue. The surface tension of an 0.1% solution in water is 18.22 dynes/cm.

Anal. Calcd for $C_{12}H_{11}F_{15}N_2O$: C, 29.76; H, 2.29, F, 58.86; N, 5.79. Found: C, 30.01; H, 2.41, F, 58.46; N, 5.82.

EXAMPLE 6

N-Methylmorpholine Perfluorooctanimide

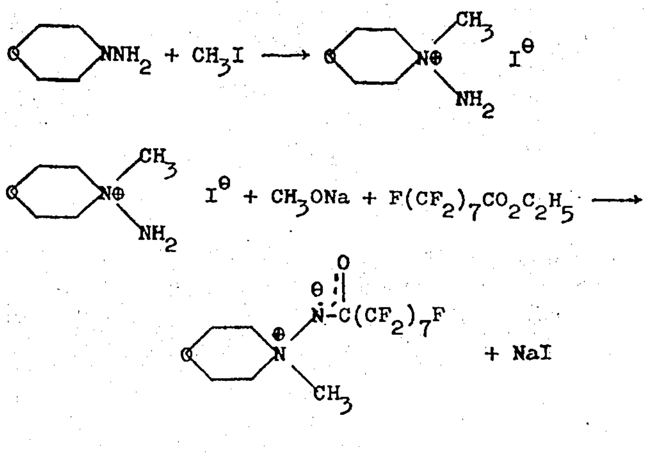

A 12.78-g (0.09 mole) sample of methyl iodide was added dropwise to a solution of 8.6 g (0.084 mole) of N-aminomorpholine in 50 ml ether. The precipitate that formed was collected on a filter, washed with ether and dried in air to give 19.73 g (96% yield) of N-amino-N-methylmorpholinium iodide as colorless crystals, mp 150°–155°(d).

Anal. Calcd for $C_5H_{13}IN_2O$: C, 24.60; H, 5.37; N, 11,48. Found: C, 24.40; H, 5.34; N, 10.68.

A mixture of 12.2 g (0.05 mole) of this iodide and 21.1 g (0.05 mole) of ethyl perfluorooctanoate was added to a solution prepared by dissolving 1.15 g (0.05 g atom) of sodium in 50 ml methanol, and the resulting reaction mixture was refluxed for 2 hr. The methanol was removed by evaporation at reduced pressure, and the residue was recrystallized from benzene to remove the sodium iodide. There was obtained 16.9 g of N-methylmorpholine perfluorooctanimide as a gummy solid, mp 50°–60°. The surface tension of an 0.1% aqueous solution is 18.24 dynes/cm.

Anal. Calcd for $C_{13}H_{13}F_{15}N_2O$: C, 30.48; H, 2.17, F, 55.64; N, 5.47. Found: C, 30.30; H, 2.27, F, 55.28; N, 5.39.

EXAMPLE 7

(2-Hydroxypropyl)dimethylamine perfluorooctanimide

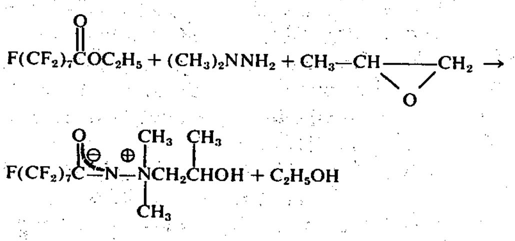

A solution of 22.1 g (0.05 mole) of ethyl perfluorooctanoate, 3.0 g (0.05 mole) of dimethylhydrazine, and 3.0 g (0.05 mole) of propylene oxide was sealed in a pressure bottle and allowed to remain at room temperature (about 25°) for 18 hr. The reaction mixture was evaporated to dryness under reduced pressure to give 25.7 g (100% yield) of a white, waxy solid, mp 67°–71°. The surface tension of an 0.1% solution in water was 22.76 dynes/cm.

Anal. Calcd for $C_{13}H_{13}F_{15}N_2O_2$: C, 30.36; H, 2.55; F, 55.42; N, 5.45. Found: C, 30.20; H, 2.53; F, 55.24; N, 5.67.

EXAMPLE 8

(2-Hydroxyethyl)dimethylamine 4,4,5,5,6,6,7,7,8,8,9,9,9-Tridecafluorononanimide

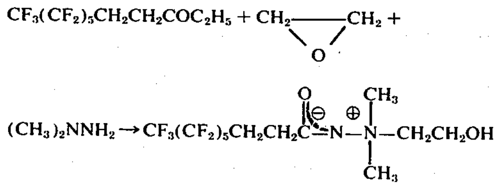

A solution of 19.75 g (0.047 mole) of ethyl 4,4,5,5,6,6,7,7,8,8,9,9,9-tridecafluorononanate, 3.0 g (0.05 mole) of 1,1-dimethylhydrazine, and 3.0 ml (0.06 mole) of ethylene oxide was refluxed for 20 hours, and then evaporated to dryness under reduced pressure. There was obtained 21.0 g of (2-hydroxyethyl)dimethylamine 4,4,5,5,6,6,7,7,8,8,9,9,9-tridecafluorononanimide as a colorless, viscous syrup, $n_D^{25}$ 1.3894. The surface tension of an 0.1% solution in water is 16.32 dynes/cm.

Anal. Calcd for $C_{13}H_{15}F_{13}N_2O_2$: C, 32.64; H, 3.16; N, 5.86; F, 51.64. Found: C, 33.13; H, 3.68; N, 6.10; F, 48.82.

EXAMPLE 9

Trimethylamine 4,4,5,5,6,6,7,7,8,8,9,9,10,10,11,11,12,12,13,13,13-Heneicosafluorotridecanimide

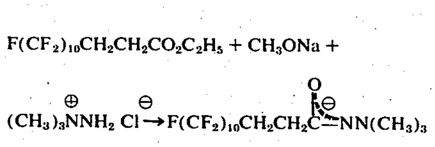

Sodium, 0.86 g (0.037 mole), was dissolved in 50 ml methanol, and 4.1 g (0.037 mole) of 1,1,1-trimethylhydrazinium chloride and 19.25 g (0.031 mole) of ethyl 4,4,5,5,6,6,7,7,8,8,9,9,10,10,11,11,12,12,13,13,13-heneicosafluorotridecane were added to the solution. The reaction mixture was refluxed for 20 hr and then cooled, mixed with 50 ml of ether, filtered. The filtrate was evaporated to dryness under reduced pressure, and the residue (18.95 g, 94% yield) was recrystallized from benzene to give trimethylamine 4,4,5,5,6,6,7,7,8,8,9,9,10,10,11,11,12,12,13,13,13-heneicosafluorotridecanimide as colorless crystals, mp 104°–106°. An 0.1% solution of this compound in water has a surface tension of 17.44 dynes/cm.

Anal. Calcd for $C_{16}H_{13}F_{21}N_2O_2$: C, 29.64; H, 2.02; F, 61.55; N, 4.32. Found: C, 29.71; H, 1.94; F, 60.86; N, 4.29.

EXAMPLE 10

$F(CF_2CF_2)_xCH_2CH_2CON^{\ominus}N^{\oplus}(CH_3)_3$

A 70.8-g sample composed of a mixture of esters having the general formula $F(CF_2CF_2)_xCH_2CH_2CO_2C_2H_5$ (approximate composition, $x = 3$, 55%; $x = 4$, 30%; $x = 5$, 10%; $x = 6$, 3.6%; $x = 7$, 0.6%; $x = 8$, trace) and a 16.9-g (0.15 mole) sample of 1,1,1-trimethylhydrazinium chloride were added to a solution prepared by dissolving 3.45 g (0.15 mole) of sodium in 200 ml methanol. The reaction mixture was refluxed for 20 hr and then cooled, mixed with 200 ml ether, and then filtered. The filtrate was evaporated to dryness under reduced pressure to give 61.67 g of the crude aminimide mixture, mp 40°–85°. An 0.1% solution of this mixture in water has a surface tension of 15.97 dynes/cm.

Anal. Found: C, 31,56; H, 2.92; F, 54.75; N, 6.06

EXAMPLE 11

$F(CF_2CF_2)_xCH_2CH_2CON^{-}N^{+}(CH_3)_2CH_2CH_2OH$

A 52-g sample of a mixture of esters having the general formula $F(CF_2CF_2)_xCH_2CH_2CO_2C_2H_5$ (approximate composition, $x = 3$, 55%; $x = 4$, 30%; $x = 5$, 10%;

$x = 6$, 3.6%; $x = 7$, 0.6%; $x = 8$, trace) was added to a solution of 7 ml (0.14 mole) ethylene oxide and 7.2 g (0.12 mole) of 1,1-dimethylhydrazine in 150 ml of methanol. The resulting solution was refluxed for 20 hr and then evaporated to dryness under reduced pressure. There was obtained 53.5 g of the aminimide mixture as a viscous amber syrup. An 0.1% solution in water has a surface tension of 16.16 dynes/cm.

Anal. Found: C, 32.20; H, 3.28; F, 52.55; N, 6.03

EXAMPLE A

Foam produced by the agitation of an 0.1% solution of trimethylamine 4,4,5,5,6,6,7,7,8,8,9,9,10,10,11,11,11-heptadecafluoroundecafluoroundecanimide in water was poured over the surface of burning hexane contained in a 500 ml beaker. The flame was extinguished.

Foam produced from 0.1% aqueous solutions of trimethylamine 4,4,5,5,6,6,7,7,8,8,9,9,9-tridecafluorononanimide, trimethylamine perfluorooctanimide, and (2-hydroxyethyl)dimethylamine perfluorooctanimide was similarly used to extinguish burning hexane.

The specific embodiments of this invention in which an exclusive property or privilege is claimed are defined by the following claims:

1. A compound having the formula

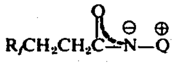

wherein $R_f$ is a straight chain fluorocarbon radical of 6 to 16 carbon atoms and $Q^+$ is derived from a water-soluble tertiary amine Q having from 3 to 6 carbon atoms and up to 3 oxygen atoms in the form of oxa or hydroxy groups.

2. A compound of claim 1 where Q is $N(CH_3)_3$.

3. A compound of claim 2 where $R_f$ is n-$C_8F_{17}$.

4. A compound of claim 2 where $R_f$ is n-$C_6F_{13}$.

5. A compound of claim 2 where $R_f$ is n-$C_{10}F_{21}$.

6. A compound of claim 1 where Q is $N(CH_3)_2CH_2CH_2OH$.

7. A compound of claim 6 where $R_f$ is n-$C_6F_{13}$.

* * * * *